(12) United States Patent  
Boutin

(10) Patent No.: US 8,230,662 B2  
(45) Date of Patent: Jul. 31, 2012

(54) MEDICATION DISPENSER SYSTEM

(75) Inventor: Jean Boutin, Longueuil (CA)

(73) Assignee: Synergie Medicale BRG Inc., Longueuil (CA)

( * ) Notice: Subject to any disclaimer, the term of this patent is extended or adjusted under 35 U.S.C. 154(b) by 265 days.

(21) Appl. No.: 12/440,522

(22) PCT Filed: Sep. 11, 2007

(86) PCT No.: PCT/CA2007/001613  
§ 371 (c)(1),  
(2), (4) Date: Mar. 9, 2009

(87) PCT Pub. No.: WO2008/031213  
PCT Pub. Date: Mar. 20, 2008

(65) Prior Publication Data  
US 2010/0042255 A1    Feb. 18, 2010

Related U.S. Application Data

(60) Provisional application No. 60/825,181, filed on Sep. 11, 2006.

(51) Int. Cl.  
*B65B 57/10*    (2006.01)  
*B65B 7/28*    (2006.01)  
*B65B 61/26*    (2006.01)  
*B65B 5/08*    (2006.01)

(52) U.S. Cl. .................. 53/55; 53/499; 53/154; 53/539; 53/131.3; 53/246; 53/281; 221/94; 221/99; 221/211; 700/242

(58) Field of Classification Search ................ 53/52, 55, 53/498, 499, 154, 539, 237, 246, 131.3, 281; 221/93, 94, 99, 211; 700/242  
See application file for complete search history.

(56) References Cited

U.S. PATENT DOCUMENTS 3,174,789 A    3/1965 Scherr  
(Continued)

FOREIGN PATENT DOCUMENTS

BE    874934    7/1979  
(Continued)

OTHER PUBLICATIONS

International Search Report, PCT/CA2007/001613, mailed Dec. 27, 2007, 5 pages.

(Continued)

*Primary Examiner* — Stephen F Gerrity  
(74) *Attorney, Agent, or Firm* — Norton Rose Canada LLP

(57) ABSTRACT

A system for filling medication dose packs with oral-solid medication items comprises storage tray drawers each having storage trays. Each storage tray stores a specific type of oral-solid medication item. The storage tray drawers are displaceable to a drawn position to expose the storage trays thereof. A table supports dose packs having a plurality of receptacles arranged in rows, with each receptacle associated with an intake time and date of a patient prescription file. A dispensing mechanism has fingers for grasping by suction an oral-solid medication item, and degrees of freedom to displace the fingers from any one of the storage trays to the dose pack, to transfer the oral-solid medication items from the storage trays in the drawn position to the receptacles of the dose pack. A dispenser controller determines the specific types of oral-solid medication items required in the receptacles of the dose pack as a function of a patient prescription file, and actuates the dispensing mechanism to control displacements and the suction thereof to fill the dose packs from the patient prescription file.

20 Claims, 8 Drawing Sheets

U.S. PATENT DOCUMENTS

| | | | |
|---|---|---|---|
| 3,609,938 A * | 10/1971 | Paddock | 53/499 |
| 3,986,638 A * | 10/1976 | DeHart | 221/211 |
| 4,655,026 A * | 4/1987 | Wigoda | 53/55 |
| 4,807,757 A | 2/1989 | Rappaport et al. | |
| 4,832,180 A * | 5/1989 | Ferrero | 198/468.3 |
| 5,152,422 A | 10/1992 | Springer | |
| 5,269,440 A | 12/1993 | Bohnert et al. | |
| 5,377,864 A * | 1/1995 | Blechl et al. | 221/99 |
| 5,405,048 A * | 4/1995 | Rogers et al. | 221/211 |
| 5,442,892 A * | 8/1995 | Burns et al. | 53/53 |
| 5,444,749 A | 8/1995 | Nambu | |
| 5,480,062 A * | 1/1996 | Rogers et al. | 221/211 |
| 5,561,970 A * | 10/1996 | Edie et al. | 53/246 |
| 5,571,258 A * | 11/1996 | Pearson | 221/211 |
| 5,788,079 A | 8/1998 | Bouthiette | |
| 5,883,806 A * | 3/1999 | Meador et al. | 221/99 |
| 6,021,623 A | 2/2000 | Bouthiette | |
| 6,023,916 A | 2/2000 | Bouthiette | |
| 6,026,726 A | 2/2000 | Bouthiette | |
| 6,115,990 A * | 9/2000 | Vogelsanger | 53/246 |
| 6,269,615 B1* | 8/2001 | Amborn et al. | 53/246 |
| 6,318,051 B1* | 11/2001 | Preiss | 53/237 |
| 6,338,007 B1* | 1/2002 | Broadfield et al. | 221/99 |
| 6,481,180 B1 | 11/2002 | Takahashi et al. | |
| 6,510,668 B2 | 1/2003 | Kim | |
| 6,581,356 B2 | 6/2003 | Kim | |
| 6,585,132 B2 | 7/2003 | Kim | |
| 6,607,094 B2* | 8/2003 | MacDonald | 221/211 |
| 6,681,935 B1 | 1/2004 | Lewis | |
| 6,805,259 B2 | 10/2004 | Stevens et al. | |
| 6,887,431 B1* | 5/2005 | Vann et al. | 221/264 |
| 7,185,476 B1 | 3/2007 | Siegel et al. | |
| 8,061,109 B2* | 11/2011 | Freudelsperger | 53/246 |
| 2002/0104291 A1* | 8/2002 | Kondou et al. | 53/443 |
| 2003/0120384 A1* | 6/2003 | Haitin et al. | 700/242 |
| 2008/0282646 A1* | 11/2008 | Gertitschke et al. | 53/244 |
| 2009/0065525 A1* | 3/2009 | Shen et al. | 221/211 |

FOREIGN PATENT DOCUMENTS

| | | |
|---|---|---|
| CA | 2207045 | 6/1997 |
| CA | 2478784 | 9/2003 |
| CA | 2478917 | 9/2003 |
| WO | WO95/00427 | 1/1995 |
| WO | WO01/74666 | 10/2001 |
| WO | WO2005/075293 | 8/2005 |

OTHER PUBLICATIONS

Healthcare Solutions, Automated Drug Management Systems, Swisslog, 2005, www.swisslog.com, 30 pages.
Pillpicker, Automated Drug Management System, Packaging, Swisslog, 2005, www.swisslog.com, 2 pages.
Supplementary European Search Report, EP07815811, Dec. 9, 2010.

* cited by examiner

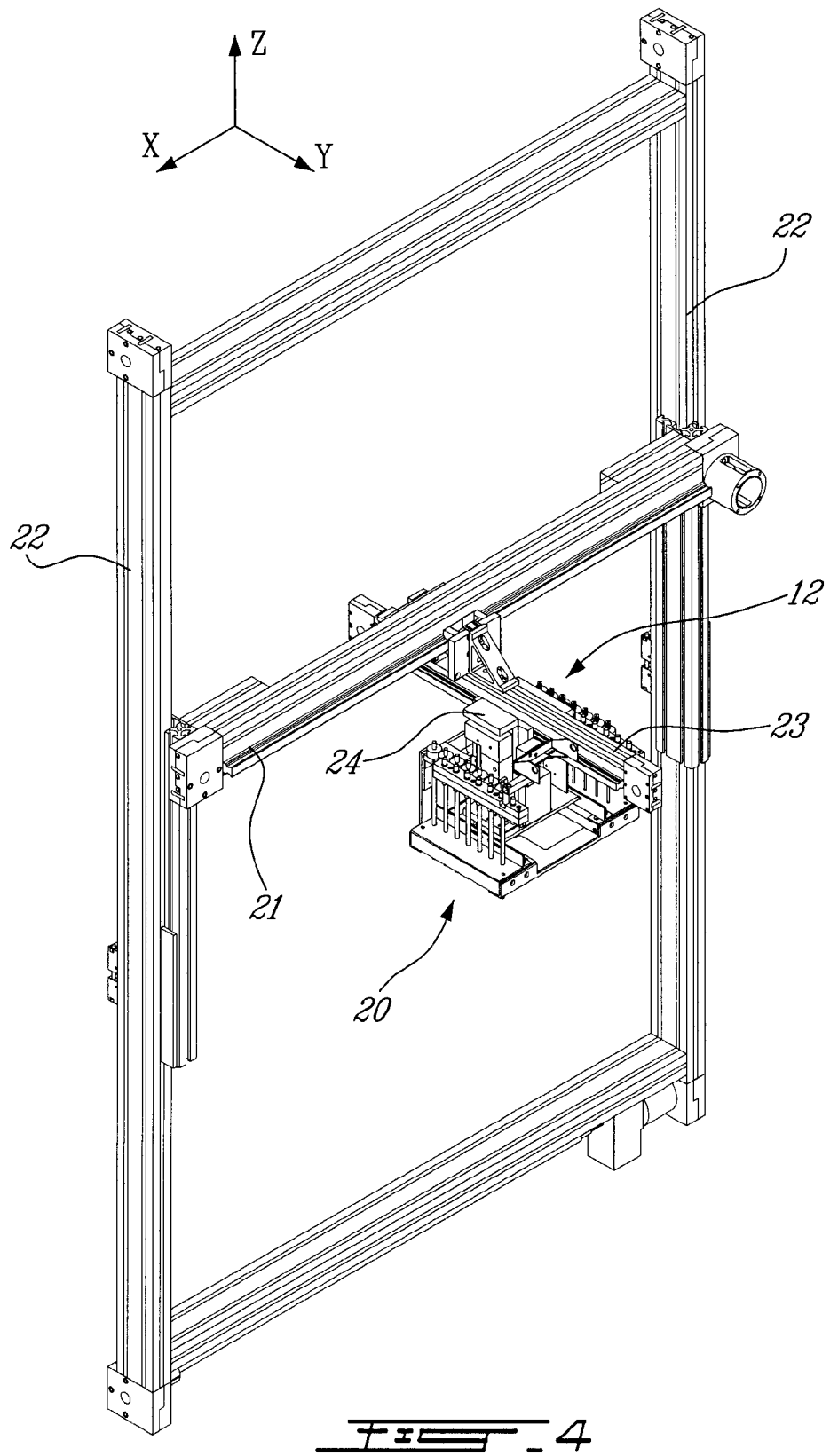

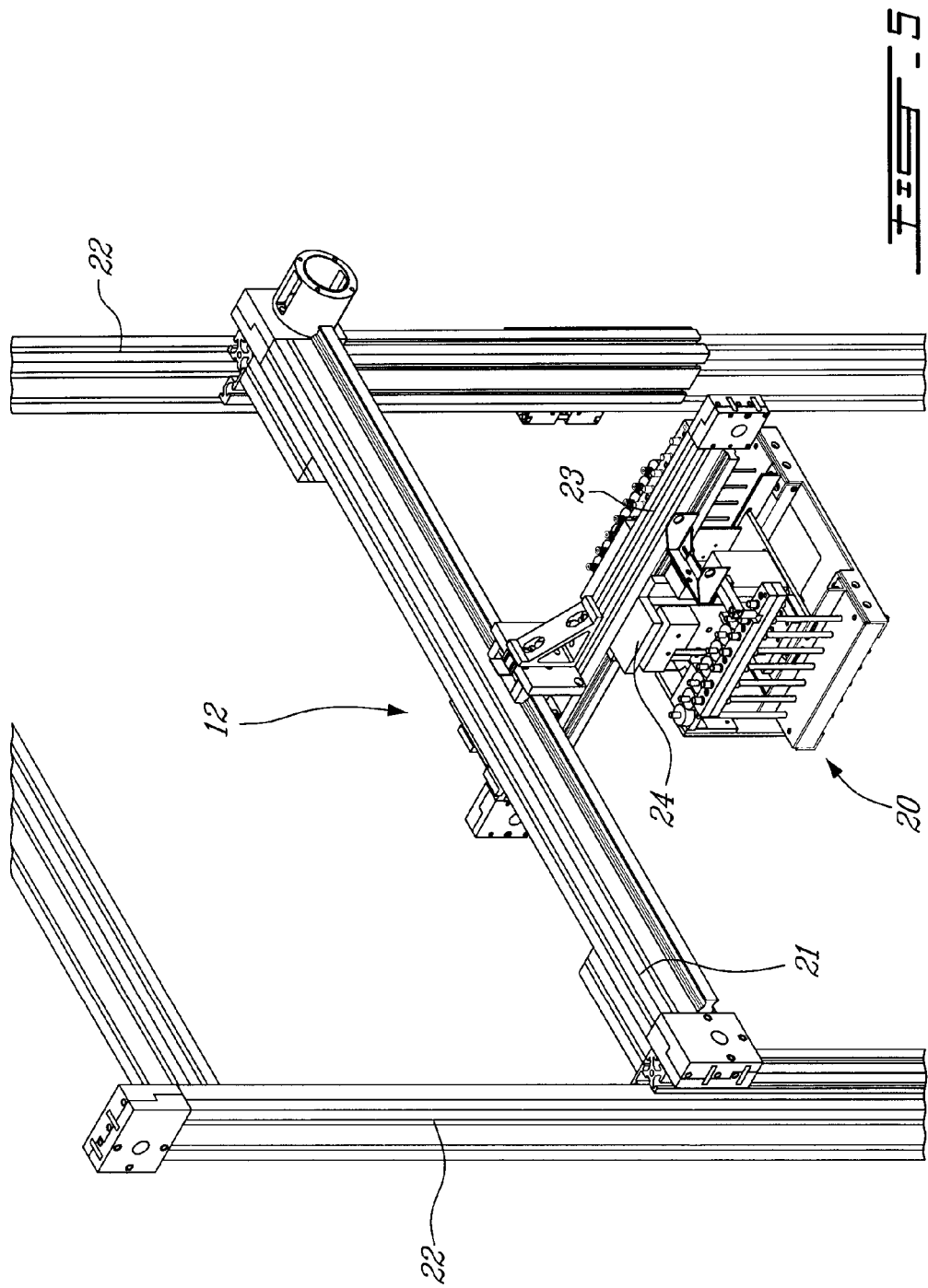

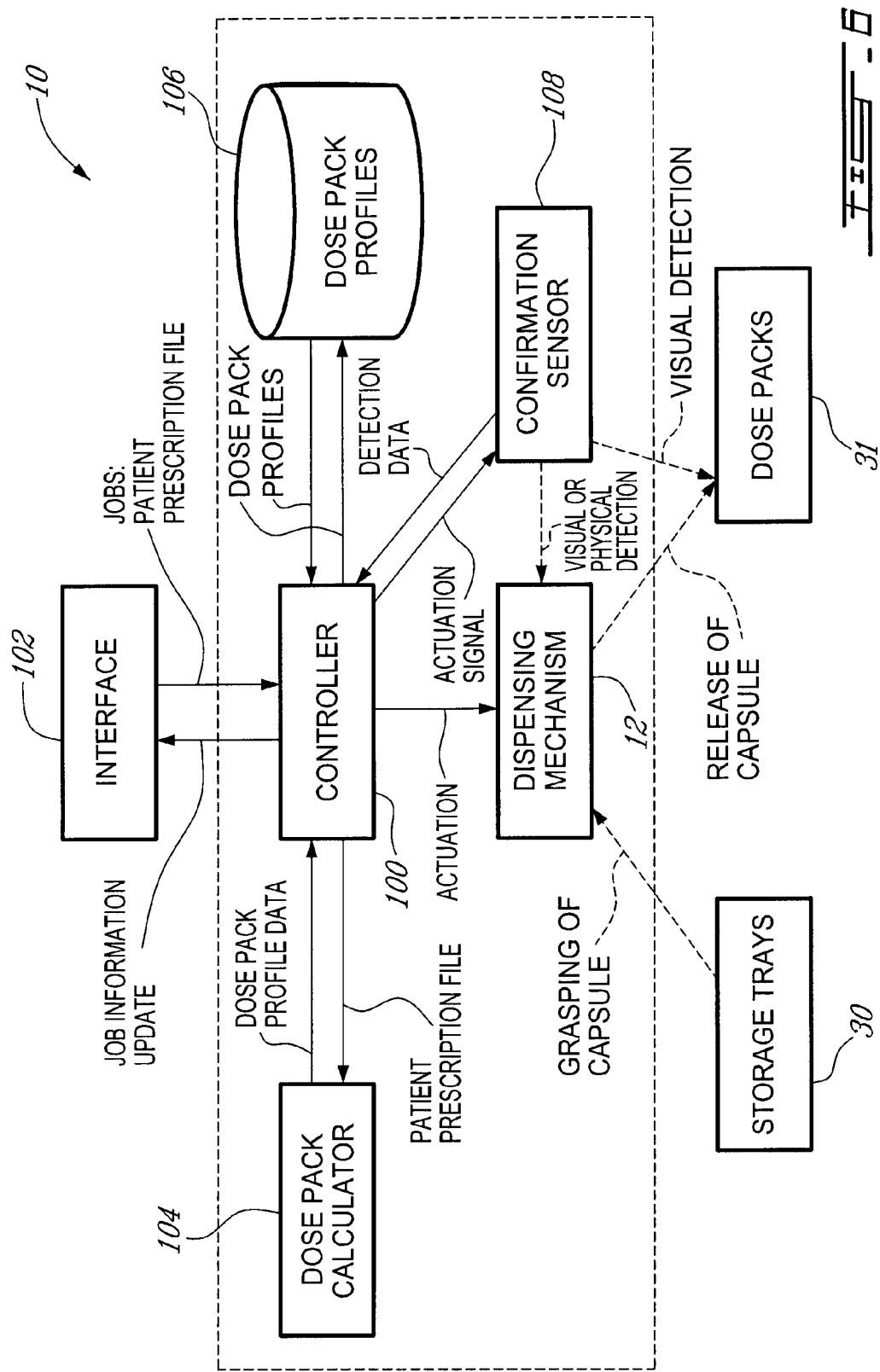

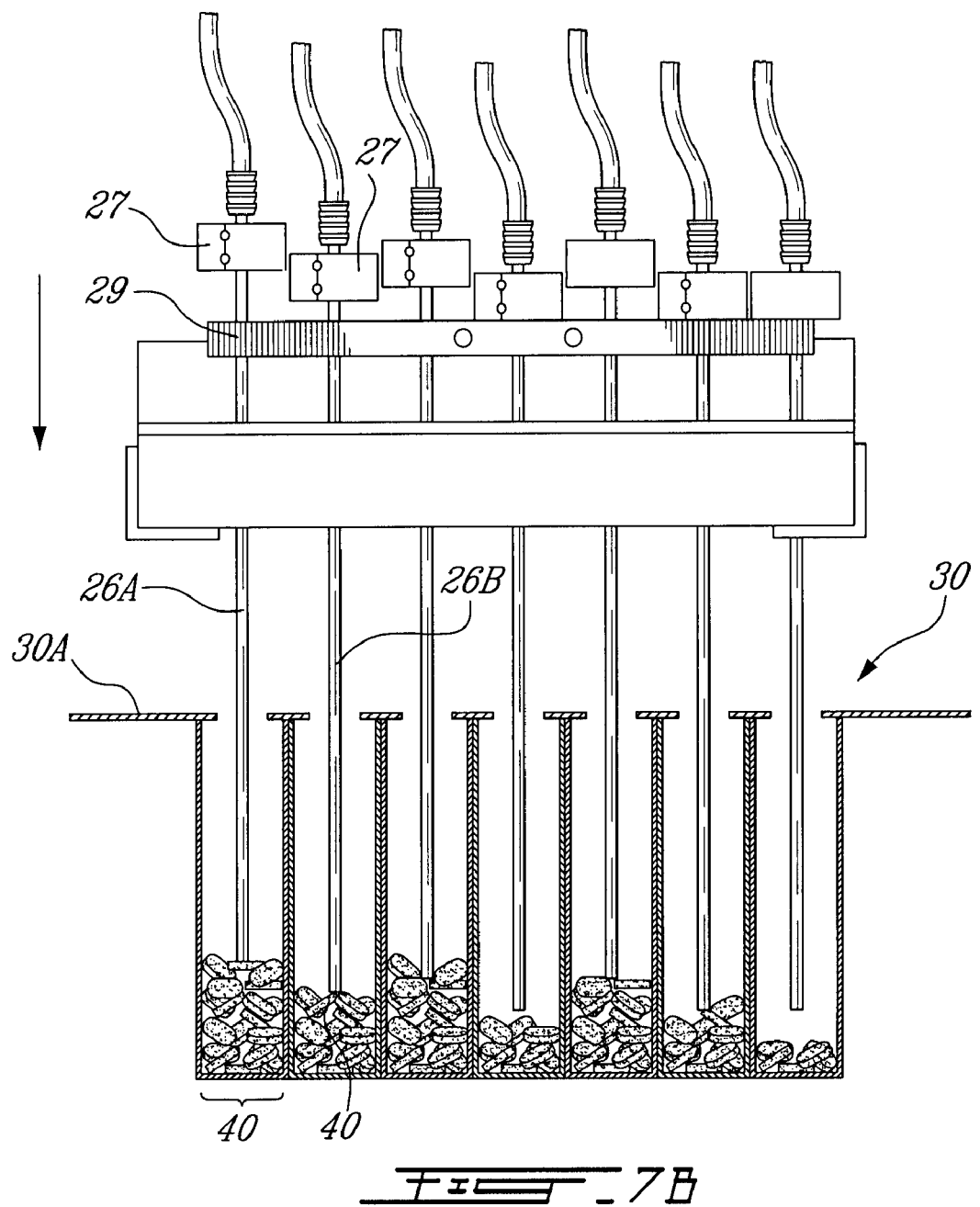

MEDICATION DISPENSER SYSTEM

CROSS-REFERENCE TO RELATED APPLICATION

This patent application claims priority on U.S. Provisional Patent Application No. 60/825,181, filed on Sep. 11, 2006.

FIELD OF THE APPLICATION

The present application generally relates to the pharmaceutical industry and, more particularly, to equipment for the packaging of medication for patients taking a plurality of different medications in tablet or capsule form.

BACKGROUND OF THE ART

Doses of medication over prescribed periods vary as a function of the type of medication and the condition of the patient. Patients are often required to take a plurality of doses over different periods of a day, and this often leads to confusion. It may be difficult for a patient to respect the prescription details (e.g., intake time, quantity) when the doses and the types of medication are numerous.

One well known method used by pharmacists to overcome this problem is to provide the patient with a dose pack having an array of receptacles, with each receptacle corresponding to a particular time of a day at which medication is to be taken. Such packs typically contain four receptacles per day for seven days, and these receptacles are in the form of sealed cups filled with appropriate medication by pharmacists as a function of the prescription, as determined by physicians' prescription.

The process of preparing these dose packs is labor-intensive, in that each receptacle must be filled individually by hand. Therefore, although the dose pack facilitates the intake of medication by patients, a substantial amount of time is required to fill these packs by pharmacists.

Accordingly, a system has been provided in order to fill such dose packs. For instance, U.S. Pat. No. 6,805,259, issued on Oct. 19, 2004, to Stevens et al., discloses a medication tablet dispenser having a plurality of stacked compartments, each containing a type of medication. The stack of compartments is vibrated so as to position oral-solid medication items in a dispensing position within the respective compartments. A funnel is positioned below the stack of compartments so as to receive a discharge of medication from the compartments. Once the funnel has the appropriate dosage of medication for a receptacle of a dose pack to be filled, the oral-solid medication items in the funnel are released into one of the receptacles. The receptacle is typically displaceable in planar translation, such that the dose pack is displaced to register a different receptacle with the funnel. The operation is repeated for each receptacle.

SUMMARY OF THE APPLICATION

It is therefore an aim of the present application to provide a novel medication dispenser system and method.

Therefore, in accordance with a first embodiment of the present application, there is provided a system for filling medication dose packs with oral-solid medication items, comprising: storage tray drawers each having at least one storage tray, with each storage tray storing a specific type of oral-solid medication item, the storage tray drawers being displaceable to a drawn position to expose, the storage trays thereof; a table supporting at least one dose pack having a plurality of receptacles arranged in rows, with each receptacle associated with an intake time and date of a patient prescription file; a dispensing mechanism having at least one finger for grasping by suction an oral-solid medication item, and degrees of freedom to displace the at least one finger from any one of the storage trays to the dose pack, to transfer the oral-solid medication items from the storage trays in the drawn position to the receptacles of the dose pack; and a dispenser controller for determining the specific types of oral-solid medication items required in the receptacles of the dose pack as a function of a patient prescription file, and for actuating the dispensing mechanism to control displacements and the suction thereof to fill the dose packs from the patient prescription file.

Further in accordance with the first embodiment of the present application, the dispensing mechanism has three translational degrees of freedom.

Further in accordance with the first embodiment of the present application, the fingers of the dispensing mechanism move along a vertical degree of freedom to grasp oral-solid medication items from the storage trays, and move along two degrees of freedom in a horizontal plane to move the fingers from the storage trays to the dose pack.

Further in accordance with the first embodiment of the present application, the vertical degree of freedom is actuated by a first degree of actuation for movement of the finger in grasping an oral-solid medication item, and by a second degree of actuation for movement of the finger from the storage trays to the dose pack.

Further in accordance with the first embodiment of the present application, the dispensing mechanism connects to the storage tray drawers to open/close the storage tray drawers to/from the drawn position.

Further in accordance with the first embodiment of the present application, the dispensing mechanism has seven of the finger, with the rows of the dose pack each having seven receptacle to represent seven days of one week.

Further in accordance with the first embodiment of the present application, the fingers of the dispensing mechanism move along a vertical degree of freedom to grasp oral-solid medication items from the storage trays, and wherein each finger has an independent suspension to absorb vertical movement once the finger has grasped a oral-solid medication item.

Further in accordance with the first embodiment of the present application, the storage trays each have openings through which the oral-solid medication items are drawn by the fingers of the dispensing mechanism, the opening being sized as a function of the dimension of the oral-solid medication item to ensure at most one of the oral-solid medication items is carried by each finger from the storage trays to the dose pack.

Further in accordance with the first embodiment of the present application, at least one sensor is provided for each said finger, for the dispenser controller to confirm that an oral-solid medication item is grasped by the finger.

Further in accordance with the first embodiment of the present application, the sensor is at least one of a pressure sensor monitoring a pressure in the finger, and an optical sensor monitoring a tip of the finger.

Further in accordance with the first embodiment of the present application, an interface produces a report identifying oral-solid medication items required to manually complete the dose pack as a function of the patient prescription file.

Further in accordance with the first embodiment of the present application, the support table has on its top surface sequential characters for each receptacle of the dose packs, and the report indicates a medication item required in a receptacle using the sequential character.

Further in accordance with the first embodiment of the present application, an interface produces a report sheet arranged in rows in accordance with the dose pack and identifying a number of oral-solid medication items in each receptacle, whereby superposing the dose pack in transparent material with the report sheet enables to see through the receptacles of the dose pack said number of oral-solid medication items required in respective ones of the receptacles of the dose pack for visual inspection.

Further in accordance with the first embodiment of the present application, the report sheet seals off the dose pack to package the medication items in the dose pack, the report sheet having a patient identification thereon.

Further in accordance with the first embodiment of the present application, the system comprises two of said table, such that a first of the tables is displaced to a verification position when filling is completed while a second one of the tables is displaced to a filling position.

Further in accordance with the first embodiment of the present application, each said storage tray drawer has a plurality of the storage trays.

Further in accordance with the first embodiment of the present application, the dispenser controller has a database to store patient prescription files.

Further in accordance with the first embodiment of the present application, the table supports a plurality of dose packs, and the dispenser controller fills the dose packs simultaneously as a function of different patient prescription files.

Further in accordance with the first embodiment of the present application, the dispensing mechanism has a plurality of the fingers to fill simultaneously a plurality of receptacles of a row of the dose pack, with the suction of each one of the fingers being actuated independently to dispense oral-solid medication items in selected ones of the receptacles of the rows.

In accordance with a second embodiment of the present application, there is provided a method for distributing oral-solid medication items from a plurality of storage trays each holding a specific type of oral-solid medication items to a dose pack divided in a plurality of receptacles arranged in rows, with each row associated with a time period, and each receptacle pack associated with an intake time of the time period, comprising: identifying the receptacles of a first row of the dose pack to receive a first type of oral-solid medication item in accordance with a patient prescription file; obtaining oral-solid medication items of the first type from an appropriate one of the storage trays; displacing the oral-solid medication items to the first row of the dose pack; and dispensing the oral-solid medication items in identified receptacles of the first row of the dose pack; wherein the steps are repeated to fill the rows of the dose pack in accordance with the patient prescription file.

Further in accordance with the second embodiment of the present application, rows of seven receptacles are provided to represent a time period of one week.

Further in accordance with the second embodiment of the present application, four of said rows by dose pack are provided to represent four intake times per day.

Further in accordance with the second embodiment of the present application, obtaining an oral-solid medication item comprises grasping by suction the oral-solid medication item.

Further in accordance with the second embodiment of the present application, grasping by suction comprises monitoring a suction pressure to ensure that an oral-solid medication item is grasped.

Further in accordance with the second embodiment of the present application, obtaining an oral-solid medication item comprises opening a storage tray drawer in which the appropriate one of the storage trays is located if the storage tray drawer is closed.

Further in accordance with the second embodiment of the present application, the steps are repeated to fill all rows of the dose pack with the first type of oral-solid medication item prior to repeating the steps for a second type of oral-solid medication item.

Further in accordance with the second embodiment of the present application, the steps are repeated to fill all rows of at least two dose packs with the first type of oral-solid medication item prior to repeating the steps for a second type of oral-solid medication item.

Further in accordance with the second embodiment of the present application, a report is produced to indicate oral-solid medication items from the patient prescription file that are not available in the storage trays.

Further in accordance with the second embodiment of the present application, outputting the report comprises indicating a sequence to manually fill a dose pack with the medication items not available in the storage trays.

Further in accordance with the second embodiment of the present application, a report is printed indicating the number of said oral-solid medication item per receptacle according to the patient prescription file, the numbers of the report being arranged in rows similarly to the dose pack for the numbers to be aligned with respective ones of the receptacles for visual inspection.

Further in accordance with the second embodiment of the present application, printing the report comprises printing the report on a sheet used to seal off the dose pack filled with medication items.

BRIEF DESCRIPTION OF DRAWINGS

FIG. 4 is a perspective view of a dispensing mechanism of the medication dispenser system of FIG. 1;

FIG. 5 is an enlarged view of the dispensing mechanism of FIG. 4; and

FIG. 6 is a block diagram of the medication dispenser system of FIG. 1;

FIG. 7B is a schematic view of the pair of fingers of the medication dispenser system with oral-solid medication items grasped by both fingers.

DESCRIPTION OF PREFERRED
EMBODIMENTS

Figure 1:
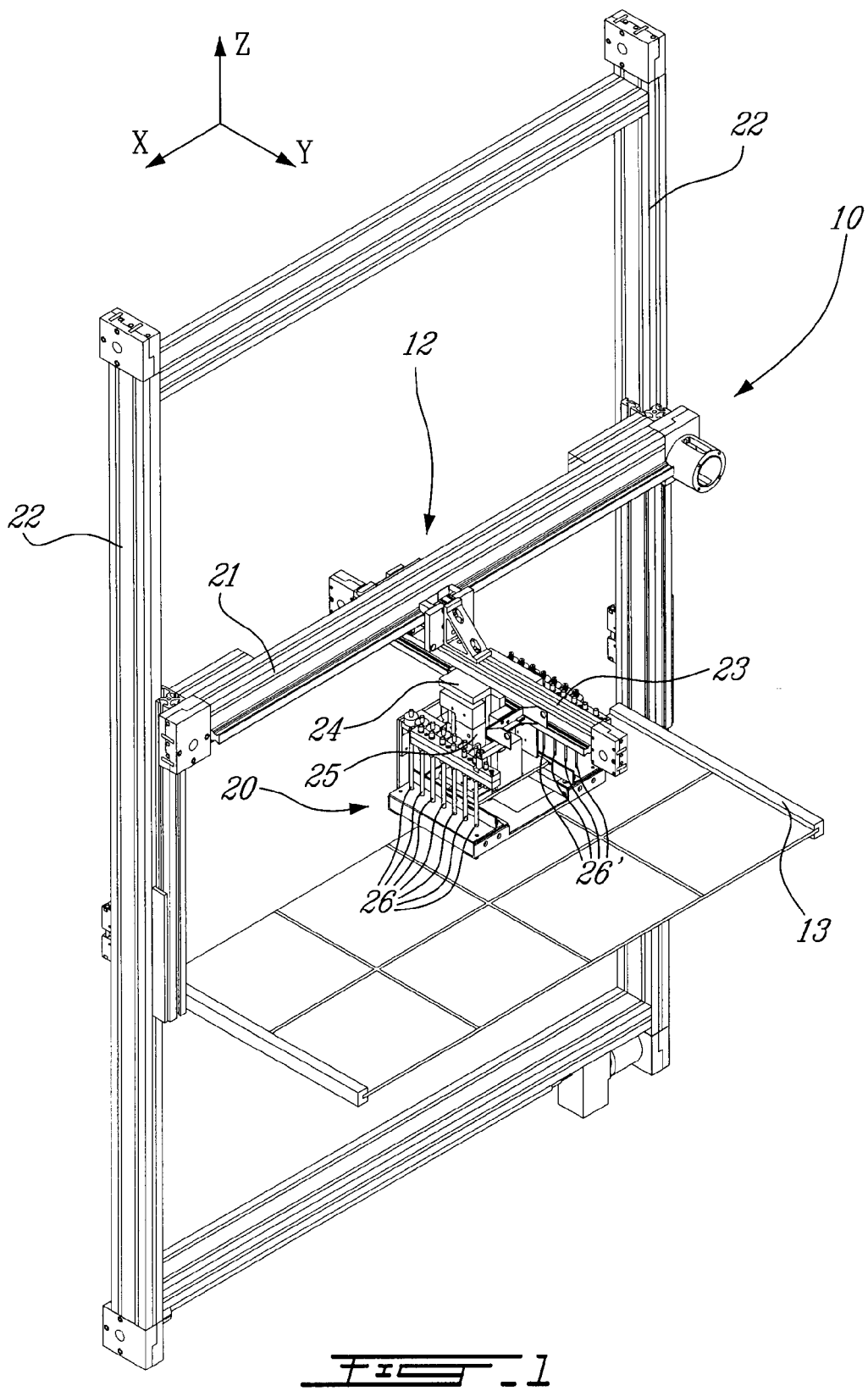
FIG. 1 is a perspective schematic view of a medication dispenser system in accordance with a preferred embodiment of the present invention.

Referring to the drawings and, more particularly, to FIG. 1, a medication dispenser system for dose packs is generally shown at 10. More specifically, a plurality of elements of the medication dispenser system 10 have been removed to illustrate a dispensing mechanism 12, and its relation with a support table 13. The support table 13 is provided to support dose packs.

In a preferred embodiment, the dispensing mechanism 12 is displaceable along three translational degrees-of-freedom (hereinafter DOF), as illustrated by directions X, Y and Z in FIG. 1. Moreover, it is contemplated to provide a translational or rotational DOF to an output arm 20 of the dispensing mechanism 12, as will be described hereinafter.

More specifically, the dispensing mechanism 12 has a first support beam 21 operatively mounted on a pair of vertical posts 22. The vertical posts 22 are typically a pair of linear actuators, with the moving portion of the linear actuators connected to opposed ends of the first support beam 21 such that the first support beam 21 is displaceable along the Z direction.

A second support beam 23 (e.g., linear actuator) is operatively connected to the first support beam 21, such that the second support beam 23 is displaceable along direction X with respect to the first support beam 21. For instance, the first support beam 21 is a linear actuator, with a moving portion of the linear actuator connected to the second support beam 23.

A carriage 24 (e.g., moving portion of a linear actuator) is mounted to the second support beam 23, and is displaceable along direction Y with respect to the second support beam 23. The carriage 24 supports the output arm 20. An actuator 25 is provided for the independent actuation of the output arm 20 with respect to a remainder of the dispensing mechanism 12. Accordingly, there are two degrees of actuation for the dispensing mechanism 12 in the vertical direction.

In a first configuration, the actuator 25 is a linear actuator providing an additional translational degree of actuation, along the Z axis. This linear actuator is preferably used for the capsule-grasping movements of the output arm 25. In such a case, the actuator 25 is advantageously smaller and more power-efficient than the linear actuators of the vertical posts 22, considering the numerous displacements to be performed by the output arm 20.

Alternatively, the actuator 25 is a rotational actuator, such that a rotational DOF is provided for the output arm 20. The actuator 20 may also combine both a translational and a rotational degree of freedom.

It is seen in FIG. 1 that the output arm 20 has two rows of seven fingers 26 (illustrated as fingers 26 and 26'). Each of the fingers 26 is provided so as to carry an oral-solid medication item or tablet (hereinafter "medication item" for simplicity purposes) from storage trays to dose packs, as will be described hereinafter. In a preferred embodiment of the present invention, the fingers 26 each have a suction tip, by which medication items are releasably connected to the fingers 26.

Alternatively, a second series of seven fingers 26' can be provided in parallel with the first series of fingers 26. In such a case, the second series of seven fingers would be of different sizes (e.g., smaller) to be capable of grasping smaller medication items. A trap (not visible) is then actuated to determine which set of the fingers 26 is moved downwardly to grasp medication items.

Figure 2:
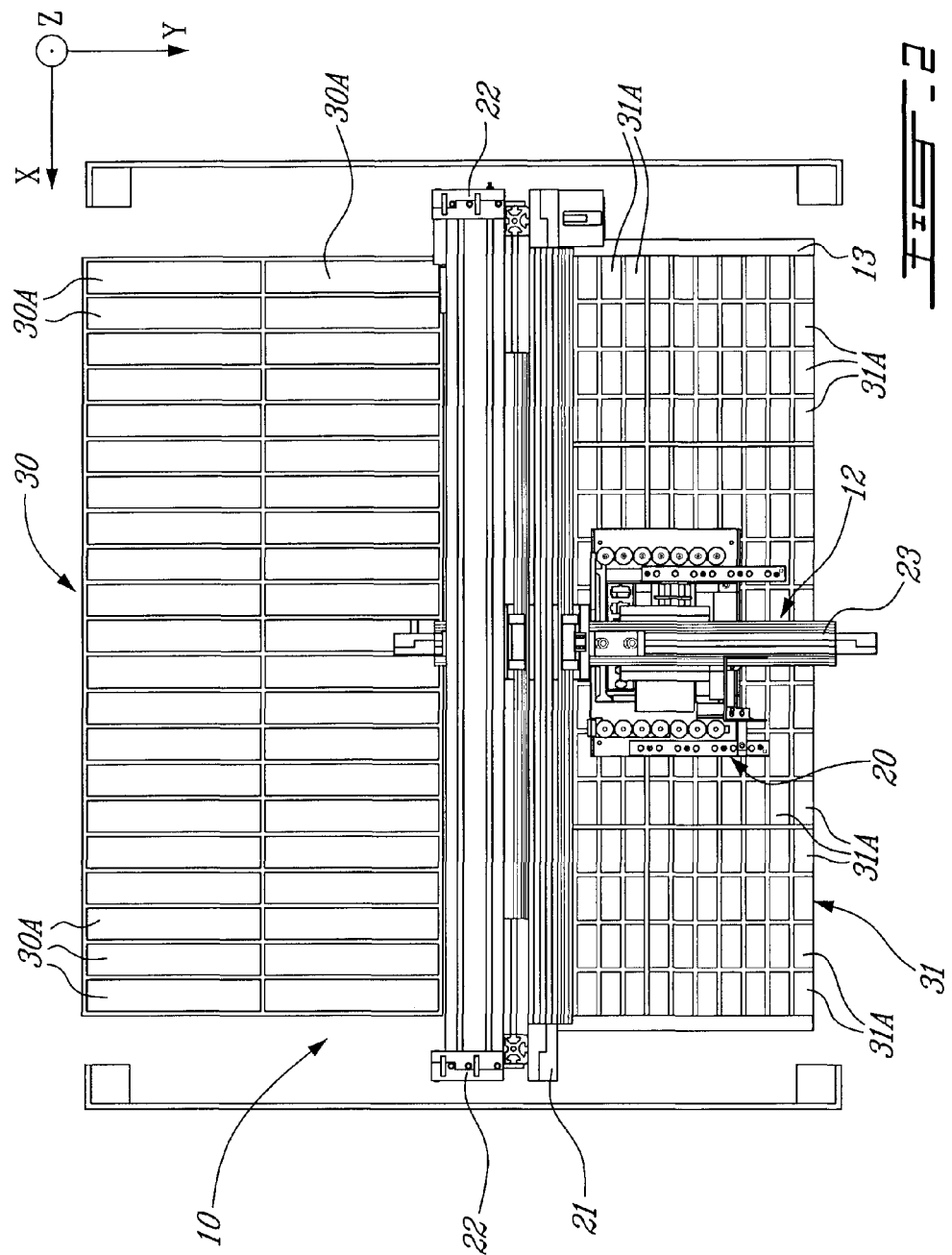
FIG. 2 is a top plan view of the medication dispenser system of FIG. 1.

Referring to FIG. 2, the medication dispenser system 10 is shown having a medication storage tray drawer 30, and a plurality (i.e., eight) of dose packs 31 on the support table 13. It is seen that the dose packs 31 have a 28-receptacle format, in that each pack 31 has 4 doses per day for a 7-day period. A few of the receptacles of the dose packs 31 are shown as 31A. It is pointed out that, although the dose packs 31 are illustrated in a 28-receptacle format, other formats of the dose pack 31 may also be used, for instance, with more or fewer than 28 receptacles.

Therefore, the output arm 20 of the dispensing mechanism 12 is displaced along the axes X, Y and Z in order to transport medication items from the medication storage tray drawer 30 to the dose packs 31.

Each of the medication storage tray drawer 30 has a plurality of storage trays (one of which is shown at 30A), each storage tray 30A containing one type of medication items. It is also contemplated to provide the storage trays with covers, which covers are perforated with openings sized as a function of the size of the medication items. Such covers would ensure that only one capsule per finger 26 exits the storage tray. Accordingly, the output arm 20 is displaced to a position above one of the storage trays 30A, whereby the fingers 26 are in position to each collect a medication item. This is as a function of the doses required in the dose packs 31, as will be discussed hereinafter.

Therefore, by the use of seven fingers 26, the receptacles of one of the dose packs 31 may all be filled simultaneously for a first time period for all seven days with one capsule of medication.

Figure 3:
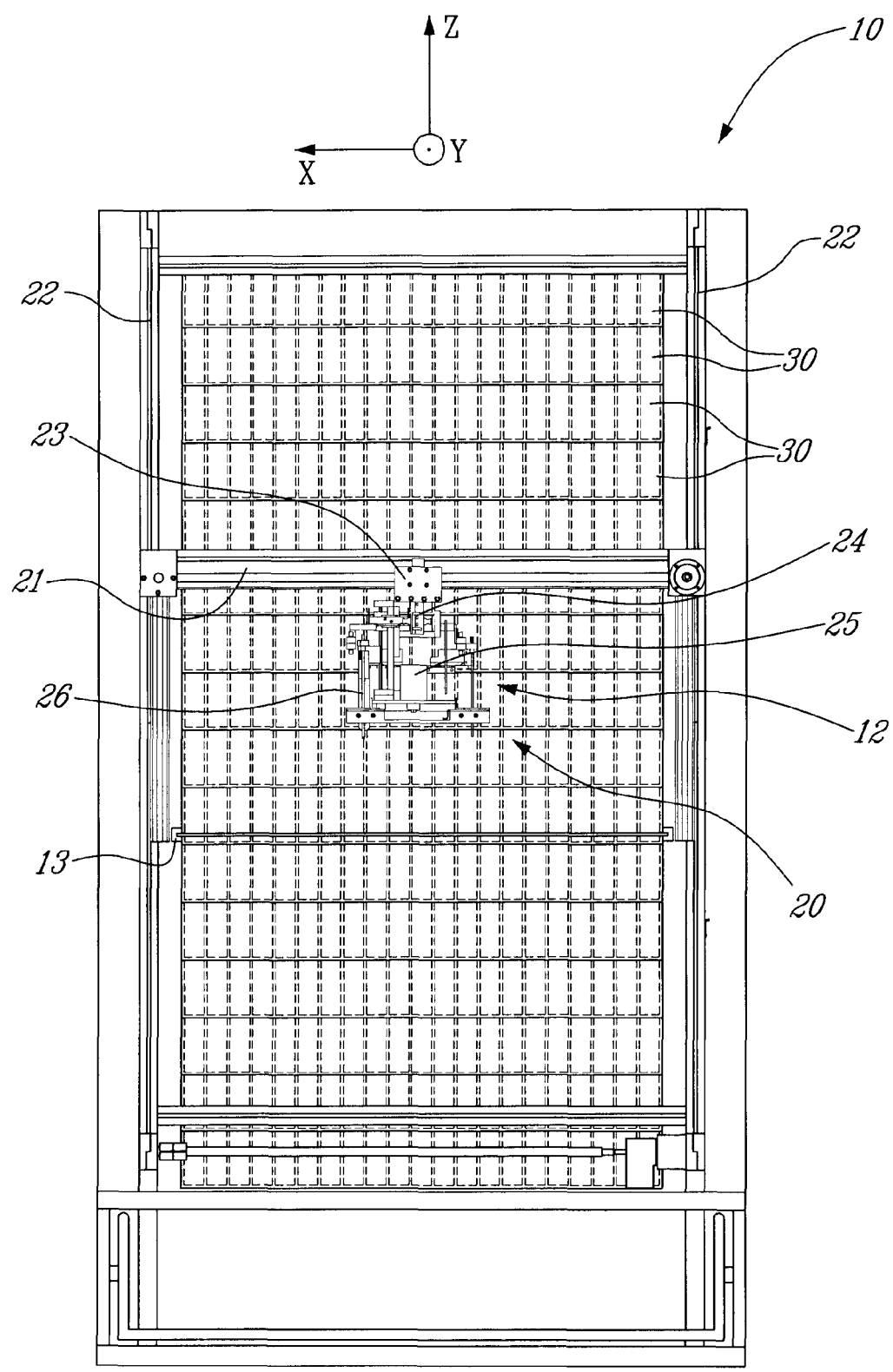
FIG. 3 is a front elevation view of the medication dispenser system of FIG. 1, with a plurality of medication storage tray drawers.

Referring to FIG. 3, the medication dispenser system 10 is shown having a plurality of medication storage tray drawers 30, stacked vertically. The medication storage tray drawers 30 are typically set back, and are displaceable to a drawn position of FIG. 2. More specifically, each of the medication storage tray drawer 30 may be translated to and from the drawn position of FIG. 2, so as to be used as a supply for the output arm 20 of the dispensing mechanism 12. The dispensing mechanism 12 is used to pull any one of the storage tray drawers 30 to a supply position (as illustrated in FIG. 2). Alternatively, the opening and closing of the storage tray drawers 30 may have its own set of actuators.

As the output arm 20 is displaceable in the Z direction as described previously, the output arm 20 travels to the height of the storage tray drawer 30 so as to collect medication items to be dropped into the appropriate dose packs 31. Once the dose packs 31 are filled with available medication from the storage trays 30, the dose packs 31 may be pulled away from the dispensing mechanism 12. More specifically, it is contemplated to provide the support table 13 with telescopic arms or a like translational mechanism in the Y axis, such that a portion of the support table 13 can readily be moved away. This configuration enables a second series of dose packs 31 to be filled while a first series of dose packs 31, pulled away from the dispensing mechanism 12, is hand-filled by the operator with medication not stored in the medication storage trays 30.

Figure 7A:
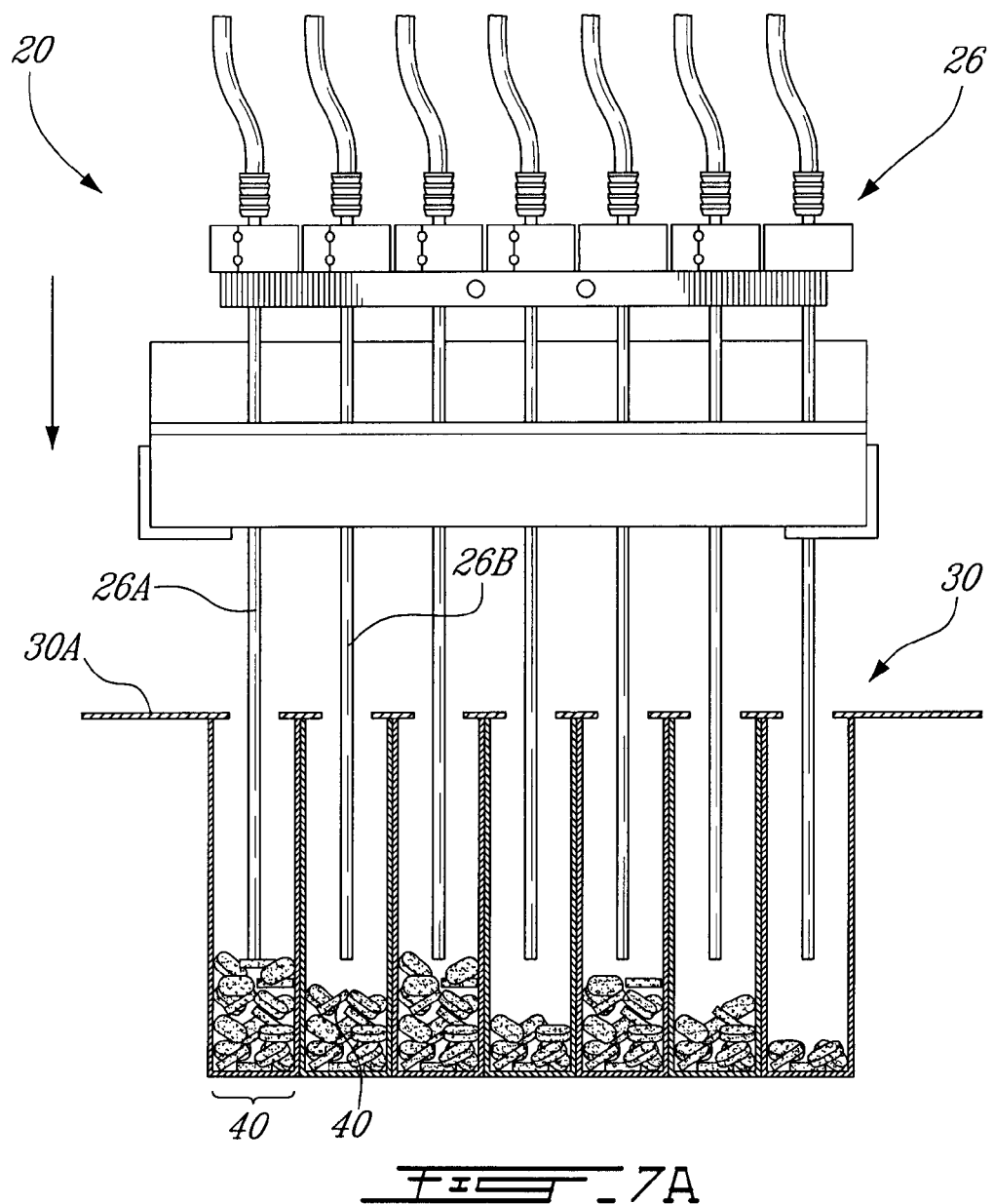
FIG. 7A is a schematic view of a pair of fingers of the medication with an oral-solid medication item grasped by one of the fingers.

Referring to FIGS. 4, 5, 7A and 7B, the dispensing mechanism 12 is shown in greater detail. There is illustrated in FIGS. 7A and 7B a pair of the fingers 26, respectively illustrated as fingers 26A and 26B in accordance with another embodiment. The fingers 26A and 26B are provided with a ring 27. Accordingly, the fingers 26 are mounted to a support 29 of the output arm 20 so as to be displaceable in translation along the Z axis, and are naturally in the position illustrated in FIG. 7A as being pulled by gravity because of the ring 27. When the fingers 26 are displaced downwardly to capture medication items 40 in the receptacles 30A of the storage trays 30, it may be required for one of the fingers 26, such as the finger 26B of FIG. 7B, to be moved lower than other finger 26, such as the finger 26A, to capture a medication item 40.

In order to stop the movement of the fingers 26 having captured a medication item, the fingers 26 are freely mounted onto the support 29 so as to be displaceable vertically, while being pulled downwardly by the effect of gravity. Accordingly, the risk of having a medication item dislodged from one of the fingers 26A is reduced by this suspension mechanism.

In a preferred embodiment, the fingers 26 are each connected to a vacuum system, such that a tip of each of the fingers 26 is subjected to a pressure differential from ambient pressure, that will be of sufficient magnitude to grasp a medication item.

The suction at the tip of each of the fingers 26 will be controlled individually, such that any combination of the fingers 26 can be actuated over the 7-day period represented by a row of the dose packs 31. This is typically performed by on/off valves between the vacuum source and the tips of the fingers 26.

It is also contemplated to provide each of the fingers 26 with pressure sensors, so as to determine whether a medication item has been grasped by the respective fingers 26, and whether the medication item has been released at the appropriate position of the output arm. It is contemplated to use other types of sensors, such as optical sensors (using LED's).

Referring to FIG. 6, a medication dispenser system 10 is shown having a controller 100 associated with the dispensing mechanism 12. The controller 100 is typically a processing unit that is programmed to operate the preparation of a plurality of dose pack jobs as a function of an inventory of medication items present in the various levels of storage trays 30 (FIG. 3), as a function of patient prescription files entered in the system 10.

The controller 100 is therefore connected to an interface 102, by which a user person (e.g., pharmacist, chemist, technician), enters various jobs. The jobs to be performed are patient prescription files in the form of oral-solid medication items to be converted into dose packs associated with the patient (i.e., customer). The jobs are typically entered as digital files, or may be entered manually through the interface 102. The interface 102 has a display screen, as well as associated peripherals, such as a keyboard, mouse, disk drives, printer, internet/ethernet ports.

A dose pack calculator 104 is also provided in association with the controller 100. The dose pack calculator 104 creates a dose pack profile from the patient prescription file. The dose pack profiles comprise: (1) an identification of the storage tray 30A from which medication items must be grasped, and (2) the receptacles 31A of each dose pack 31 in which the medication items will be received. Accordingly, the dispensing mechanism 12 receives a series of maneuver instructions to fill the dose packs. The dose pack calculator 104 is associated with the controller 100 which actuates the dispensing mechanism as a function of the dose pack profiles.

A database 106 is provided in association with the controller 100, such that the various jobs (i.e., patient prescription files having been converted to dose pack profiles) may be stored in the wait of being performed. It is contemplated to store dose pack profiles of specific customers, in such a way that a customer's identification may be the only information required through the interface 102 to order the preparation of a dose pack from the controller 100 for that customer.

A confirmation sensor 108 is connected to the controller 100 and is actuated as a function of commands from the controller 100. The confirmation sensor 108 is provided to determine whether a medication item has been dispensed into a prescribed receptacle 31A. The detection data is sent to the controller 100 by the confirmation sensor 108, whereby the controller 100 will update its accounting of the medication items dispensed in a job.

The confirmation sensor 108 may take various configurations. For instance, it has been described previously that the fingers 26 may be provided with a pressure sensor. The confirmation sensor 108 may be such pressure sensors, with pressure profiles being fed to the controller 100 has detection data. The pressure profiles are then interpreted by the dose pack calculator 106 to determine whether the medication item has been successfully dispensed in the appropriate dose pack 31.

Alternatively or additionally, the confirmation sensor 108 may be a visual or optical sensor, that is configured to detect the dispensing of a medication item into a prescribed receptacle 31A, so as to confirm that a medication item has been dispensed.

The controller 100 is connected to the dispensing mechanism 12 so as to actuate the DOFs and the suction of the dispensing mechanism 12. More specifically, the controller 100, by way of its association with the dose pack calculator 104, will convert dose pack profiles into a plurality of actuation commands of the dispensing mechanism 12. More specifically, as a function of the position and level of the medication into the storage trays 30A of the storage tray drawers 30, the controller 100 will actuate the linear and rotational actuators of the dispensing mechanism 12 as well as the grasping action of the fingers 26, so as to dispense appropriate medication items into the prescribed receptacles 31A of the dose packs 31.

Therefore, in order to perform a job associated with a single patient prescription file, the medication dispenser system 10 will obtain the prescription file from the interface 102 or from the database 104.

The patient prescription file is converted by the controller 100, in association with the dose pack calculator 104, into a dose pack profile comprising a plurality of displacements and actuations of the dispensing mechanism 12, as a function of the position of the medication items in the various storage trays 30A (FIG. 3), and of the position of the dose packs 31 on the support table 13.

The dispensing mechanism 12 will then proceed to the displacement of medication from the storage trays 30A to the dose pack 31, with the confirmation sensor 108 confirming that a medication item was appropriately dispensed as prescribed.

The controller 100 will account the detection data from the confirmation sensor 108. The inventory data of the dose pack provided by the controller 100 will result in feedback as to the completion of the job.

The medication dispenser system 10 advantageously has the capacity of displacing a plurality of medication items at once. More specifically, it has been observed that prescriptions often require a same medication item to be taken over a 7-day period at a same period of a day. The dispensing mechanism 12 therefore has the capacity of grasping seven medication items in one displacement from the storage tray drawer 30 to the dose packs 31. Alternatively, the rotational DOF of the output arm 20 could be used to grasp medication items from different trays 30A of a same storage tray drawer 30.

In order to minimize the number of movements performed by the dispensing mechanism 12, and therefore accelerate the completion of the jobs, it is considered to proceed by filling all receptacles 31A of all dose packs 31 with a first type of medication item. Accordingly, the appropriate storage tray drawer 30 is opened once, and the distribution of a first type of medication from that storage tray drawer 30 is performed for all rows of the dose packs 31. Once the distribution of the first type of medication is completed, the distribution of the medication for a second type of medication item is performed, from the same storage tray drawer 30. These steps are performed until all types of medication items from that same storage tray drawer 30 have been distributed. The dispensing mechanism 12 then switches to another storage tray drawer 30.

Some types of medication may be absent from the storage trays 30. In such cases, it is contemplated to manually fill the dose packs with such medication before or after the preparation of the dose pack with the medication dispenser system 10. A report is typically produced to indicate what medication items are absent from the storage tray 30 to complete the job. The report typically contains a sequence to follow to fill the dose pack. In an embodiment, the support table 13 has on its surface an array of sequential numbers sized such that each receptacle 31A on the support table 13 has its own location identified with one of the sequential numbers. The report identifies the receptacles 31A with their sequential number, and indicates what medication item is required in the identified receptacles 31A.

In order to verify the contents of a filled dose pack, one contemplated solution is to have the interface 102 print out a report sheet that is arranged in an array representing the arrangement of receptacles 31A of the dose pack 31, for every completed job, with the report sheet featuring the number of medication items required in each receptacle. As the dose packs 31 are typically made of a transparent material, the report sheet is superposed with the filled dose pack in such a way that the receptacles 31A are in register with the respective number of items. Accordingly, by seeing the number through the receptacle 31A, the user can determine if the number of items in the receptacle 31A matches with the number seen through the receptacle 31A. In an embodiment, the report sheet is the sheet used to seal off the filled dose pack. Accordingly, verification can be performed when the dose pack is filled and sealed.

It is suggested to have appropriate personnel review the jobs performed with the dose packs, to ensure that the prescriptions have been respected. For instance, the interface 102 preferably has a printer, such that a check list could be printed out for the review of the contents of a dose pack by a pharmacist prior to the dose pack being sealed off.

In order to refill the storage trays 30A, it is considered to operate with bar codes as a safety measure. For instance, the user may be required to scan a bar code on each storage tray drawer 30, on each storage tray 30A and on the refill container prior to a refill. The medication dispenser system 10 then executes a comparison between bar codes to confirm that the storage tray can be refilled with the contents of the container.

The invention claimed is:

1. A system for filling medication dose packs with oral-solid medication items, comprising:
    at least one storage tray, with the at least one storage tray storing a specific type of oral-solid medication item;
    a table supporting at least one dose pack having a plurality of receptacles arranged in rows, with each receptacle associated with an intake time and date of a patient prescription file;
    a dispensing mechanism having at least two fingers each for grasping by suction an oral-solid medication item, and degrees of freedom to displace the at least two fingers from the at least one storage tray to the dose pack, to transfer the oral-solid medication items from the at least one storage tray to the receptacles of the dose pack; and
    a dispenser controller for determining the specific types of oral-solid medication items required in the receptacles of the dose pack as a function of a patient prescription file, and for actuating the dispensing mechanism to control displacements and the suction thereof to fill the dose packs from the patient prescription file, the suction of each one of the fingers being actuated independently to selectively grasp and dispense one unit of the oral-solid medication items with only one of the two fingers while at least another of the fingers is concurrently unactuated in suction to grasp and dispense oral-solid medication items.

2. The system according to claim 1, wherein the dispensing mechanism has three translational degrees of freedom.

3. The system according to claim 1, wherein the fingers of the dispensing mechanism move along a vertical degree of freedom to grasp oral-solid medication items from the at least one storage tray, and move along two degrees of freedom in a horizontal plane to move the fingers from the at least one storage tray to the dose pack.

4. The system according to claim 3, wherein the vertical degree of freedom is actuated by a first degree of actuation for movement of the fingers in grasping an oral-solid medication item, and by a second degree of actuation for movement of the fingers from the at least one storage trays- to the dose pack.

5. The system according to claim 1, wherein the dispensing mechanism has seven of the fingers, with the rows of the dose pack each having seven receptacles to represent seven days of one week.

6. The system according to claim 5, wherein the fingers of the dispensing mechanism move along a vertical degree of freedom to grasp oral-solid medication items from the at least one storage tray, and wherein each said finger has an independent suspension to absorb vertical movement once the finger has grasped a oral-solid medication item.

7. The system according to claim 1, further comprising a plurality of the at least one storage tray, with each said storage tray storing an own type of oral-solid medication item, wherein the storage trays each have openings through which the oral-solid medication items are drawn by the fingers of the dispensing mechanism, the opening being sized as a function of the dimension of the oral-solid medication item to ensure at most one of the oral-solid medication items is carried by each said finger from the storage trays to the dose pack.

8. The system according to claim 1, further comprising at least one sensor for each said finger, for the dispenser controller to confirm that an oral-solid medication item is grasped by the finger.

9. The system according to claim 8, wherein the sensor is at least one of a pressure sensor monitoring a pressure in the finger, and an optical sensor monitoring a tip of the finger.

10. The system according to claim 1, further comprising an interface producing a report identifying oral-solid medication items required to manually complete the dose pack as a function of the patient prescription file.

11. The system according to claim 10, wherein the support table has on its top surface sequential characters for each receptacle of the dose packs, and the report indicates a medication item required in a receptacle using the sequential character.

12. The system according to claim 1, further comprising an interface producing a report sheet arranged in rows in accordance with the dose pack and identifying a number of oral-solid medication items in each receptacle, whereby superposing the dose pack in transparent material with the report sheet enables to see through the receptacles of the dose pack said number of oral-solid medication items required in respective ones of the receptacles of the dose pack for visual inspection.

13. The system according to claim 12, wherein said report sheet seals off the dose pack to package the medication items in the dose pack, the report sheet having a patient identification thereon.

14. The system according to claim 1, comprising two of said tables, such that a first of the tables is displaced to a verification position when filling is completed while a second one of the tables is displaced to a filling position.

15. The system according to claim 1, wherein the dispenser controller has a database to store patient prescription files.

16. The system according to claim 1, wherein the table supports a plurality of dose packs, and the dispenser controller fills the dose packs simultaneously as a function of different patient prescription files.

17. The system according to claim 1, further comprising storage tray drawers being displaceable to a drawn position, with each said storage tray drawer supporting at least one storage tray, the storage tray drawers displaced to the drawn position to expose the storage trays thereof.

18. The system according to claim 17, wherein the dispensing mechanism connects to the storage tray drawers to open/close the storage tray drawers to/from the drawn position.

19. The system according to claim 17, wherein each said storage tray drawer has a plurality of the storage trays.

20. A system for filling medication dose packs with oral-solid medication items, comprising:

storage tray drawers each having at least one storage tray, with each storage tray storing a specific type of oral-solid medication item, the storage tray drawers being displaceable to a drawn position to expose the storage trays thereof;

a table supporting at least one dose pack having a plurality of receptacles arranged in rows, with each receptacle associated with an intake time and date of a patient prescription file;

a dispensing mechanism having at least one finger for grasping by suction an oral-solid medication item, and degrees of freedom to displace the at least one finger from any one of the storage trays to the dose pack, to transfer the oral-solid medication items from the storage trays in the drawn position to the receptacles of the dose pack; and a dispenser controller for determining the specific types of oral-solid medication items required in the receptacles of the dose pack as a function of a patient prescription file, and for actuating the dispensing mechanism to control displacements and the suction thereof to fill the dose packs from the patient prescription file.

\* \* \* \* \*